(12) United States Patent
Mao et al.

(10) Patent No.: US 7,145,023 B2
(45) Date of Patent: Dec. 5, 2006

(54) PROCESSES FOR PREPARING SOLID TOCOPHEROL SUCCINATE CALCIUM AND MAGNESIUM SALTS

(75) Inventors: Jianhua Mao, West Chester, OH (US); Sang I. Kang, Bourbonnais, IL (US)

(73) Assignee: Cognis Corporation, Cincinnati, OH (US)

( * ) Notice: Subject to any disclaimer, the term of this patent is extended or adjusted under 35 U.S.C. 154(b) by 0 days.

(21) Appl. No.: 10/991,259

(22) Filed: Nov. 17, 2004

(65) Prior Publication Data

US 2005/0124826 A1    Jun. 9, 2005

Related U.S. Application Data

(60) Provisional application No. 60/523,869, filed on Nov. 20, 2003.

(51) Int. Cl.
*C07D 311/72*    (2006.01)

(52) U.S. Cl. .................................................. 549/412
(58) Field of Classification Search ................ 549/412
See application file for complete search history.

(56) References Cited

U.S. PATENT DOCUMENTS

| 2,407,726 A | 9/1946 | Smith et al. |
| 3,432,525 A | 3/1969 | Kijima et al. |

FOREIGN PATENT DOCUMENTS

| JP | 50105812 | 2/1974 |
| JP | 11092474 | 4/1999 |

*Primary Examiner*—Taofiq Solola
(74) *Attorney, Agent, or Firm*—John F. Daniels; Arthur G. Seifert

(57) ABSTRACT

Processes for preparing salts of alcohol polybasic acid partial esters are described wherein an alcohol polybasic acid partial ester is reacted with a compound selected from the group consisting of metal oxides, metal hydroxides, metal carbonates and mixtures thereof.

18 Claims, No Drawings

PROCESSES FOR PREPARING SOLID TOCOPHEROL SUCCINATE CALCIUM AND MAGNESIUM SALTS

CROSS-REFERENCE TO RELATED APPLICATIONS

This application claims priority, under 35 U.S.C. §119(e), of U.S. Provisional Patent Application No. 60/523,869, filed on Nov. 20, 2003, the entire contents of which are hereby incorporated by reference.

BACKGROUND OF THE INVENTION

Concerns over maintaining healthy lifestyles continue to grow, and accordingly, vitamin and antioxidant use and intake also continue to rise. As more evidence of the potential benefits associated with the use and intake of vitamins and antioxidants continues to be generated, demand for such substances increases, as does the demand for various forms thereof. Many naturally derived antioxidants and vitamins are normally delivered as oily substances or viscous liquids for encapsulation. However, many potential applications for increased, beneficial consumption and use of such vitamins and antioxidants make solid, free-flowing, and/or powdery formulations more desirable.

For example, some tocopherol compounds such as free tocopherol and tocopheryl acetate, which are oily liquids that exhibit vitamin E activity, can be mixed with carriers and other additives to be made into solids. Other ester forms of tocopherol, such as tocopheryl succinate, are solid. Unfortunately, solid forms of tocopherol such as tocopheryl succinate still do not adequately meet all of the applicational demands necessitated by the various forms of desired vitamin consumption, including, for example, compaction for tableting. Tocopherol compound salts, and in particular, salts of dibasic acid hemiesters of tocopherol, provide tocopherol compounds that exhibit favorable formulation properties. One specific example of such a salt is the calcium salt of tocopherol succinate. However, existing methods for producing such salts from dibasic acid hemiester and calcium starting materials are costly, complicated, and/or inefficient, and thus not widely employed to produce such compounds for use in the vitamin market.

Known processes for producing tocopherol calcium succinate include two step processes wherein a starting material such as tocopherol succinic acid is reacted with lithium hydroxide to produce the lithium salt of tocopherol succinate, which is then reacted with a calcium compound to exchange the lithium ion with a calcium ion. Other processes react tocopherol succinic acid with calcium carboxylates in aqueous solutions to attempt to achieve adequate reaction, but separation of the product from residual carboxylic acid is less than ideal and the reaction is slow.

Thus, there is a need in the art for a process by which tocopherol calcium succinate and other beneficial tocopherol compound salts can be prepared in high yield both quickly and cost-effectively, without undesirable impurities.

SUMMARY OF THE INVENTION

The present invention relates, in general, to processes for preparing salts of alcohol polybasic acid partial esters. As used herein, the term polybasic refers to any compound having two or more carboxylic acid functionalities and thus includes both dibasic acids and higher functionality polybasic acids. Also, as used herein, the term partial ester refers to any polybasic acid having one or more esterified carboxylic acid groups and one or more unesterified carboxylic acid groups.

More particularly, preferred embodiments of the present invention relate to processes for preparing divalent metal salts of tocopherol dibasic acid hemiesters. It has been surprisingly found that salts of alcohol polybasic acid partial esters can be easily and efficiently made via a reaction between an alcohol polybasic acid partial ester and a metal compound selected from the group consisting of metal oxides, metal hydroxides, metal carbonates and mixtures thereof. Metal oxides and metal hydroxides are preferred. Surprisingly, in comparison to other metal reactants, metal oxides and hydroxides produce the salts in near quantitative yields. Moreover, the processes in accordance with the present invention do not produce unwanted by-products or undesirable impurities.

The present invention includes a process for preparing a salt of an alcohol polybasic acid partial ester, the process comprising: (a) providing an alcohol polybasic acid partial ester; and (b) reacting the alcohol polybasic acid partial ester with a metal compound selected from the group consisting of metal oxides, metal hydroxides, metal carbonates and mixtures thereof. Preferred metal compounds include oxides, hydroxides and carbonates of divalent metals. More preferred are oxides, hydroxides and carbonates of the alkaline earth metals. In certain preferred embodiments of the present invention, the compound comprises an oxide, hydroxide and/or carbonate of a metal selected from the group consisting of calcium, magnesium and zinc. In each of these progressively more preferred, embodiments, oxides and hydroxides are most preferred.

In various preferred embodiments of the present invention, the alcohol polybasic acid partial ester comprises an alcohol dibasic acid hemiester. A preferred alcohol dibasic acid hemiester comprises a tocopherol dibasic acid hemiester. In even more preferred embodiments of the present invention, the alcohol dibasic acid hemiester comprises a d-α-tocopherol dibasic acid hemiester. In the most preferred embodiments of the present invention, the alcohol dibasic acid hemiester comprises d-α-tocopherol succinate.

A particularly preferred embodiment of the present invention includes a process for preparing a calcium salt of a tocopherol dibasic acid hemiester, the process comprising: (a) providing d-α-tocopherol succinate; and (b) reacting the d-α-tocopherol succinate with a compound selected from the group consisting of calcium oxide and calcium hydroxide.

DETAILED DESCRIPTION OF THE INVENTION

The present invention includes processes for preparing salts of alcohol polybasic acid partial esters. Salts prepared by processes according to the present invention correspond to the general formula (I):

$$[M^{m+}]_n[X^{n-}]_m \qquad (I)$$

wherein M represents a metal cation having a positive charge of m where m is a number of from 2 to 6, and X represents an alcohol polybasic acid partial ester anion wherein n is a number of from 1 to 5 and represents the number of unesterified carboxylic acid groups. In preferred embodiments of the present invention m represents a number of from 2 to 4, and most preferably, m equals 2. In other preferred embodiments of the present invention n represents a number of from 1 to 3, and most preferably 1. In certain preferred embodiments of the present invention m represents a number of from 2 to 4, and most preferably, m equals 2, and n represents a number of from 1 to 3, and most preferably n equals 1.

Alcohol polybasic acid partial ester starting materials which are useful in the processes according to the present invention include reaction products of alcohols and polybasic acids. Suitable alcohols can be monohydric or polyhydric, can be branched, linear or cyclic, can be primary, secondary or tertiary, and can be aliphatic or aromatic. Any carboxylic acid having two or more carboxylic acid groups can be employed.

In preferred embodiments of the present invention, the alcohol polybasic acid partial ester starting material comprises an alcohol dibasic acid hemiester. Suitable alcohol dibasic acid hemiesters correspond to the general formula (II):

R—O$^\alpha$(O)—R$^1$—(O)OH  (II)

wherein R—O$^\alpha$ represents a deprotonated alcohol moiety based upon an alcohol of the formula RO$^\alpha$H, and R$^1$ represents a divalent hydrocarbon group having from 2 to 44 carbon atoms which can be linear, branched, cyclic or polycyclic, aliphatic or aromatic; and saturated or unsaturated, wherein RO$^\alpha$H comprises an alcohol having at least one hydroxyl moiety O$^\alpha$H, and R represents a hydrocarbon moiety having from 1 to 40 carbon atoms which can be linear, branched, cyclic or polycyclic, aliphatic or aromatic, and saturated or unsaturated. Alcohols of the formula RO$^\alpha$H can be primary, secondary or tertiary, and can be aliphatic or aromatic. Suitable alcohols include bioactive alcohols such as chromanol-derivatives, including tocopherols and tocotrienols, and retinols, as well as steroidal alcohols, such as phytosterols. In certain preferred embodiments of the present invention, RO$^\alpha$H represents a chromanol derivative such as a tocopherol or tocotrienol.

Accordingly, suitable alcohol polybasic acid partial esters for use in the processes according to the present invention can be prepared by esterifying an alcohol of the formula R(O$^\alpha$H)$_x$ and a polybasic acid of the formula, R$^1$—[C(O)OH]$_y$, or anhydrides thereof; wherein R(O$^\alpha$H) is as defined above and x represents a number of from 1 to 5, preferably 1 to 3 and most preferably 1; and wherein R$^1$ is as defined above and y represents a number of from 2 to 5, preferably 2 to 3 and most preferably 2. In various preferred embodiments of the present invention wherein the alcohol polybasic acid partial ester comprises an-alcohol dibasic acid hemiester, suitable alcohol dibasic acid hemiesters can be prepared by esterifying an alcohol of the formula RO$^\alpha$H and a dibasic acid of the formula, HO(O)—R$^1$—(O)OH; wherein R$^1$ represents a divalent hydrocarbon group having from 2 to 44 carbon atoms, preferably 2 to 18 carbon atoms. The alcohol and the dibasic acid are esterified in a ratio such that one of the carboxylic acid moieties is esterified leaving a dibasic acid hemiester, such as those corresponding to the general formula (II) set forth above. Preparative esterification procedures suitable for esterifying an alcohol of the formula RO$^\alpha$H and a dibasic acid of the formula, HO(O)—R$^\alpha$—(O)OH are known in the art and include any known preparative method for esterifying an alcohol and an acid, such as direct esterification and transesterification using suitable catalysts. For example, an alcohol and a dibasic acid can be reacted in the presence of an acidic catalyst to produce the ester product thereof. A suitable molar ratio of alcohol to dibasic acid for the preparation of the dibasic acid hemiester is about 1:1.

Dibasic acid components useful for preparing the dibasic acid hemiesters used as starting materials in processes according to preferred embodiments of the present invention preferably include $C_2$–$C_{18}$ dicarboxylic acids and their anhydrides. The dicarboxylic acids may be straight or branched, saturated or unsaturated. The acids may be substituted with, for example, an α-hydroxy moiety. Examples of suitable dicarboxylic acids for use in preparing the dibasic acid hemiesters used as tocopherol starting materials in the processes of the present invention include malonic acid, succinic acid, pentadienoic acid, hexadienoic acid, heptadienoic acid, maleic acid, fumaric acid, azelaic acid, dodecanedioic acid, octadecanedioic acid, and the anhydrides thereof. The preferred dibasic acid component for use in preparing alcohol dibasic acid hemiesters for use in processes according to certain preferred embodiments of the present invention is succinic acid and/or succinic anhydride. Polybasic acids having three or more carboxylic acid groups which may be used to prepare polybasic acid partial esters for use in accordance with various embodiments of the present invention include, for example, citric acid, ethylenediamine tetraacetic acid (EDTA), and diethylene triamine pentaacetic acid (DTPA).

In certain more preferred embodiments of the present invention, the alcohol dibasic acid hemiester comprises a dibasic acid hemiester of a chromanol compound such as a tocopherol or tocotrienol. In other words, in certain preferred embodiments of the present invention, the alcohol, RO$^\alpha$H, represents a chromanol compound of the general formula (III):

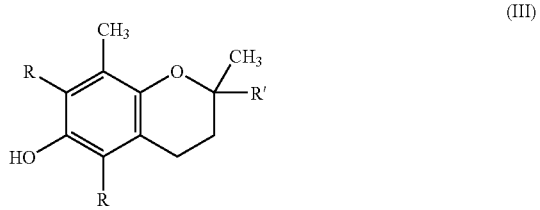

wherein each R independently represents a hydrogen atom or a methyl group and R' represents a hydrocarbon chain having from 1 to 24 carbon atoms which may be linear or branched, and saturated or unsaturated. In such preferred embodiments of the present invention wherein the alcohol, RO$^\alpha$H, represents a chromanol compound selected from tocopherols and tocotrienols, the esterification product resulting from the esterification of the chromanol compound and the dibasic acid is referred to as a tocopherol dibasic acid hemiester.

Tocopherol dibasic acid hemiester starting materials which are useful in the processes according to the present invention are based upon dibasic acid hemiesters of one or more tocopherol compounds. As used herein, the term "tocopherol compounds" refers to the broad class of compounds that can be characterized as derivatives of 6-chromanol having an isoprenoid side chain, of which many are known to exhibit vitamin E activity. These compounds include, for example, the alpha (α-), beta (β-), gamma (γ-) and delta (δ-)homologues of tocopherol, as well as unsaturated derivatives, such as, tocomonoenols, tocodienols and tocotrienols. The tocopherol dibasic acid hemiester starting materials which are useful in the processes according to the present invention may be synthetic or naturally-derived, and may include either optical enantiomer of any of the aforementioned homologues, or mixtures thereof. In preferred embodiments of the present invention, naturally-derived tocopherol starting materials are used. Preferably the tocopherol starting materials used in the processes according to the present invention include d-α-tocopherol compounds, most preferably d-α-tocopherol succinic acid. Mixtures of naturally-derived tocopherols may also be used, such as, for example, mixtures of alpha (α-), beta (β-), gamma (γ-) and/or delta (δ-)tocopherol.

The tocopherol dibasic acid hemiesters which can be used as starting materials in the processes of the present invention can be obtained commercially from various sources such as Cognis Corporation, available as Covitol® 1210 natural d-α-tocopherol succinic acid, but may also be prepared by reacting one or more tocopherol compounds and a dibasic component selected from dibasic acids, dibasic acid anhydrides, and dibasic acid halides. A preferred route for preparing tocopherol succinic acid for use in the present invention is the direct esterification of d-α-tocopherol with succinic anhydride.

The present invention comprises providing an alcohol polybasic acid partial ester; and reacting the alcohol polybasic acid partial ester with a metal compound selected from the group consisting of metal oxides, metal hydroxides, metal carbonates and mixtures thereof. The alcohol polybasic acid partial ester may be provided for reaction in solution. Preferred solvents for alcohol polybasic acid partial esters to be used in accordance with the present invention include $C_1$–$C_4$ monohydric alcohols, polyols, alkyl acetates, aldehydes, ketones, water and mixtures thereof. The less polar the solvent, the lower the solubility of the alcohol polybasic acid partial esters therein. For example, the solubility of the partial ester starting materials in pure propanol or butanol may be too low to be practical. However, water is also a suitable solvent for alcohol polybasic acid partial esters, such as tocopherol succinate, and may be combined with less polar alcohol solvents in small amounts to provide suitable solubility for the ester materials. However, water is a product of the reaction between the partial ester and the metal oxide/metal hydroxide and may shift the reaction equilibrium unfavorably towards the reactants. On the other hand, water can be advantageously employed as a cosolvent when the metal compound comprises a metal carbonate and increases yield in such situations. An especially preferred solvent for providing a solution of an alcohol dibasic acid hemiester comprises methanol, and more preferably methanol with a water content below 0.5% by weight. In a particularly preferred embodiment of the present invention, providing an alcohol dibasic acid hemiester comprises combining and mixing tocopherol succinic acid and methanol. In even more preferred embodiments of the present invention, the tocopherol succinic acid comprises d-α-tocopherol succinic acid.

The present invention also comprises reacting an alcohol polybasic acid partial ester with a compound selected from the group consisting of metal oxides, metal hydroxides, metal carbonates and mixtures thereof. Preferred oxides, hydroxides and/or carbonates for use in the processes according to the present invention include oxides, hydroxides and/or carbonates of divalent metals. More preferred are the oxides, hydroxides and/or carbonates of alkaline earth metals. A group of particularly preferred metal oxides, hydroxides and/or carbonates includes those based on calcium, magnesium and zinc. The most preferred oxide, hydroxide and carbonate are calcium oxide, calcium hydroxide and calcium carbonate. Again, in each of these progressively more preferred embodiments of the present invention, metal oxides and metal hydroxides are preferred due to improved yield. However, through the use of water as a cosolvent, yields obtained through the use of metal carbonates can be improved.

The metal compounds used in accordance with the present invention can be obtained commercially from a variety of sources. Calcium oxide which can be used in certain preferred embodiments of the present invention can be obtained commercially as well, or can be derived from calcium carbonate (limestone) by applying heat necessary to drive off any carbon dioxide present. Other preferred metal compounds include calcium hydroxide, magnesium hydroxide, zinc oxide and zinc hydroxide which can also be obtained commercially.

The metal compound can be combined with the alcohol polybasic acid partial ester prior to reaction, or gradually added during the reaction. The metal compound is preferably added prior to reaction and in certain preferred embodiments of the present invention, the metal compound is combined with the alcohol polybasic acid partial ester in the solvent described above prior to reaction.

The metal compound and alcohol polybasic acid partial ester are preferably combined for reaction in an equivalent ratio greater than 1:1. In more preferred embodiments of the present invention, the metal compound and the alcohol polybasic acid partial ester are combined for reaction in an equivalent ratio of 1.05:1 or greater, and more preferably in an equivalent ratio of 1.1:1 or greater. In certain other preferred embodiments of the present invention, the metal compound and the alcohol polybasic acid partial ester are combined for reaction in an equivalent ratio of 1.2:1 or greater. As various metal compounds and various alcohol polybasic acid partial esters may be employed in the present invention, the reactive equivalents provided by the chosen reactants may vary. For example, each mole of calcium oxide, or any divalent metal compound, provides two reactive equivalents, and a trivalent metal provides three, and so on. An alcohol dibasic acid hemiester has a single reactive carboxylate moiety, whereas a monoester of citric acid has two reactive carboxylate moieties. Thus, for example reacting 0.5 moles of calcium oxide and 1.0 moles of tocopherol succinic acid hemiester results in a metal to hemiester equivalent ratio of 1:1.

Reacting the metal compound and the alcohol polybasic acid partial ester in accordance with the present invention can be accomplished in a variety of reactor types. Preferably, a batch reactor of suitable size, &quipped with a stirring device can be used. The metal compound, the alcohol polybasic acid partial ester and any solvent are combined and reacted over a period of time. In accordance with certain preferred embodiments of the present invention, the reaction is carried out at a temperature of from about 20 to 100° C. In more preferred embodiments of the present invention, the reaction is carried out at a temperature of from about 30 to 75° C. A most preferred reaction temperature is from about 40 to 70° C. The reaction of the metal compound and the alcohol polybasic acid partial ester in accordance with the present invention can be carried out over a period of time ranging from minutes to hours, and depends upon factors such as the reaction temperature, reaction solvent, and reactor size and type. In certain preferred embodiments of the present invention, the reaction can be carried out over a period of from about 1 to 4 hours, more preferably about 2 hours.

After the reaction, the reaction product, which contains the metal salt of the alcohol polybasic acid partial ester, solvent and any residual reactants, is preferably cooled to about room temperature and then filtered to separate the solid product from the solvent and reactants. Preferably, the solid product can also be washed after filtration with additional quantities of the solvent used during the reaction, or any other suitable solvent.

The filtered and washed product can now preferably be dried to remove any residual solvent. Drying can be performed through evaporation, or preferably in any suitable apparatus, such as, for example, an oven or rotary dryer.

In certain preferred embodiments of the present invention wherein the alcohol polybasic acid partial ester comprises tocopherol succinic acid and the metal compound is a calcium salt, drying should be performed at temperatures below 100° C. to avoid discoloration. Drying times can vary based upon the amount of residual solvent. After drying, the product can ground or milled to meet various particle size requirements.

The present invention will now be illustrated in more detail by reference to the following specific, non-limiting examples.

EXAMPLE 1

Preparation of α-Tocopheryl Calcium Succinate (TCS)

1.1. Reactor: 500-mL 3 or 4-necked round bottomed flask with a condenser, a thermocouple and a mechanical stirrer.

1.2. Raw Materials: α-tocopheryl succinic acid ("TSA", Cognis Corp.), anhydrous calcium hydroxide (98+%, Acros), and methanol (HPLC grade). The methanol contained from 0.01% to 0.05% water.

TABLE 1

| Material | MW (g/mol) | Quantity(g)/Moles |
|---|---|---|
| TSA | 530.5 | 53.08/0.100 |
| Calcium hydroxide | 74.09 | 4.07/0.055 |
| Methanol | 32.04 | (100 + 40)g |

Note:
Molecular weight of the expected product TCS, 1100.0 g/mol 1.3. Experimental Procedure
(1) The 500 mL three-neck round bottom flask is charged with 53.08 g TSA (0.100 mol), 4.07 g calcium hydroxide (0.055 mol) and 100 g methanol at ambient. temperature.
(2) The agitator is activated at 300 rpm and the mixture is heated to 60° C.
(3) The reaction mixture is held at about 60° C. for about two hours.
(4) After the two hours, the reactor is cooled to a temperature of about 40–45° C.
(5) The solid product is filtered on a Buchner funnel (diameter 9 cm) with #4 Whatman filter paper.
(6) The reaction flask is rinsed with 20 g methanol and the solid product is washed with methanol (20 g×2).
(7) The "wet" product is placed into a 500-mL freeze dryer and is dried-by rotary evaporating at 55–70° C./26" Hg for up to about 10 hours.

EXAMPLE 2

53.2 g (0.100 moles) of d-α-tocopherol succinic acid (TSA) and 250 ml of methanol were combined in a 500 ml 3-neck glass flask, which was equipped with a mechanical stirrer, a thermometer, and a condenser. The mixture was heated to about 30° C. The TSA dissolved in the methanol at about 28° C. Subsequently, 3.15 g (0.056 moles) of calcium oxide were added to the flask at about 30° C. In this example, 0.100 moles of TSA and 0.056 moles of calcium oxide equates to a $Ca^{2+}$/TSA equivalent ratio of (0.056·2):0.100, or 1.120. The reaction temperature was then raised to about 58–60° C., and held in that temperature range for about 2 hours. The reaction mixture was then allowed to cool to room temperature (about 25° C.). The solid product was removed from the methanol by filtration, and dried under vacuum (≈100 mm Hg) at 50–55° C. for about 24 hours. The solid was analyzed via infrared spectrometry, calcium analysis and solubility testing and determined to be the calcium salt of tocopherol succinate. 51.3 g of the product were obtained.

EXAMPLE 3

53.07 g (0.100 moles) of d-α-tocopherol succinic acid (TSA), 4.11 g (0.05545 moles) of calcium hydroxide (Ca(OH)$_2$) and 230 ml of methanol were placed in a 500 ml 3-neck glass flask, which was equipped with a mechanical stirrer, a thermometer, and a condenser. In this example, 0.100 moles of TSA and 0.055 moles of calcium hydroxide equates to a $Ca^{2+}$/TSA equivalent ratio of (0.05545·2):0.100, or 1.109. The reaction temperature was then raised to about 58–60° C., and held in that temperature range for about 2 hours. The reaction mixture was then allowed to cool to room temperature (about 25° C.). The solid product was removed from the methanol by filtration. The solid product was dried under vacuum (≈100 mm Hg) at 50–55° C. for 24 hours. The solid was analyzed via infrared spectrometry, calcium analysis and solubility testing and determined to be the calcium salt of tocopherol succinate. 54.4 g product were obtained.

EXAMPLES 4–16

Tocopherol succinic acid (TSA) and the oxide/hydroxide/carbonate reagent listed in Table 2 below were combined in methanol in the corresponding $Ca^{2+}$/TSA equivalent ratio listed in Table 2 and reacted at about 58–60° C. for about 2 hours. After cooling, the solid product in each example was removed from the methanol by filtration. The solid product was dried under vacuum (≈100 mm Hg) at 50–55° C. for 24 hours. The solid was analyzed via infrared spectrometry, calcium analysis and solubility testing and determined to be the calcium salt of tocopherol succinate. The weight of the tocopherol calcium succinate obtained in each example along with the yield is listed below in Table 2.

TABLE 2

| Example | Calcium Salts | $Ca^{2+}$/TSA Equiv. Ratio | TCS Weight, (g) | Yield, (%) |
|---|---|---|---|---|
| 4 | CaO | 1.033 | 52.1 | 94.73 |
| 5 | CaO | 1.011 | 48.5 | 88.18 |
| 6 | CaO | 1.008 | 49.8 | 90.55 |
| 7 | CaO | 1.067 | 50.6 | 92.00 |
| 8 | CaO | 1.154 | 52.2 | 94.91 |
| 9 | CaO | 1.202 | 53.1 | 96.55 |
| 10 | Ca(OH)$_2$ | 1.052 | 52.1 | 94.73 |
| 11 | Ca(OH)$_2$ | 1.111 | 53.8 | 97.82 |
| 12 | Ca(OH)$_2$ | 1.150 | 55.3 | 100.55 |
| 13 | Ca(OH)$_2$ | 1.206 | 57.7 | 104.91 |
| 14 | Ca(OH)$_2$ | 1.110 | 55.9 | 101.60 |

TABLE 2-continued

| Example | Calcium Salts | Ca$^{2+}$/TSA Equiv. Ratio | TCS Weight, (g) | Yield, (%) |
|---|---|---|---|---|
| 15 | Ca(OH)$_2$ | 1.106 | 55.5 | 100.82 |
| 16 | CaCO$_3$ | 1.006 | 42.0 | 76.36 |

As can be seen from Table 2, the yield of tocopherol calcium succinate obtained is very good. Additionally, when using an oxide/hydroxide metal compound the yields are even more improved. Near quantitative yields are obtained using calcium oxide and calcium hydroxide without degradation of the starting material, d-α-tocopherol succinic acid. HPLC analysis revealed that in each example less than 0.1% d-α-tocopherol succinic acid underwent hydrolysis reverting back to d-α-tocopherol. Although metal carbonates, such as calcium carbonate employed in Example 16, are generally inferior to metal oxides and metal hydroxides, their performance is still greatly improved over other metal reagents and their overall yield can be improved to nearly equivalent to that of oxides and hydroxides at least in part through the use of water as a cosolvent.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A process for preparing d-α-tocopherol calcium succinate, the process comprising:
   (a) providing d-α-tocopherol succinate; and
   (b) reacting the d-α-tocopherol succinate with an equivalent excess of a metal compound selected from the group consisting of calcium oxide and calcium hydroxide at a temperature of from 50 to 70° C. in a liquid solvent comprising a monohydric C1–4 alcohol with or without water as a co-solvent.

2. The process according to claim 1, wherein the liquid solvent is methanol without water as a co-solvent.

3. The process according to claim 1, wherein the liquid solvent is methanol which contains less than 0.5% water.

4. The process according to claim 1, wherein the metal compound is reacted with tocopherol succinate or mixture of tocopherol succinates in an equivalent ratio of 1.1:1 or greater.

5. A process for preparing a tocopherol metal succinate, the process comprising:
   (a) providing a tocopherol succinate or a mixture of tocopherol succinates; and
   (b) reacting the tocopherol succinate or a mixture of tocopherol succinates with an equivalent excess of a metal compound selected from the group consisting of calcium oxide, calcium hydroxide, calcium carbonate, magnesium oxide, magnesium hydroxide and zinc oxide at a temperature of from 50 to 70° C. in a liquid solvent comprising a monohydric C1–4 alcohol with or without water as a co-solvent.

6. The process according to claim 5, wherein the tocopherol is selected from alpha (α-), beta (β-), gamma (γ-) and delta (δ-) homologues of tocopherol, tocomonoenols, tocodienols and tocotrienols and mixtures thereof.

7. The process according to claim 5, wherein the tocopherol is a naturally derived tocopherol.

8. The process according to claim 5, wherein the tocopherol is d-α-tocopherol.

9. The process according to claim 5, wherein the metal compound is calcium oxide or calcium hydroxide.

10. The process according to claim 5, wherein the liquid solvent is methanol without water as a co-solvent.

11. The process according to claim 5, wherein the liquid solvent is methanol which contains less than 0.5% water.

12. The process according to claim 5, wherein the metal compound is reacted with the tocopherol succinate or mixture of tocopherol succinates in an equivalent ratio 1.05:1 or greater.

13. The process according to claim 7, wherein the metal compound is calcium oxide or calcium hydroxide and is reacted with the naturally derived tocopherol succinate in an equivalent ratio of 1.1:1 or greater.

14. The process according to claim 13, further comprising recovering the solid d-α-tocopherol calcium succinate product of step (b) by filtration.

15. The process according to claim 5, further comprising recovering the solid tocopherol metal succinate product of step (b) by filtration.

16. A process for preparing solid d-α-tocopherol calcium succinate, the process comprising:
   (a) providing d-α-tocopherol succinate; and
   (b) reacting the d-α-tocopherol succinate with an equivalent excess of a metal compound selected from the group consisting of calcium hydroxide at a temperature of from 50 to 70° C. in a liquid solvent comprising methanol, and
   (c) filtering the reaction mixture to recover the solid d-α-tocopherol calcium succinate.

17. The process according to claim 16, wherein the methanol contains less than 0.5% water.

18. The process according to claim 16, wherein the metal compound is reacted with the tocopherol succinate or mixture of tocopherol succinate in an equivalent ratio of 1.1:1 or greater.

* * * * *